US00PP09924P

United States Patent [19]

Jones

[11] Patent Number: Plant 9,924

[45] Date of Patent: Jun. 17, 1997

[54] BLACK WALNUT TREE NAMES STW-13

[75] Inventor: James E. Jones, Stockton, Mo.

[73] Assignee: Charles Sheppard, Springfield, Mo.

[21] Appl. No.: 617,625

[22] Filed: Mar. 18, 1996

[51] Int. Cl.[6] ..... A01H 5/00

[52] U.S. Cl. ..... Plt./32

[58] Field of Search ..... Plt./32

*Primary Examiner*—James R. Feyrer

*Attorney, Agent, or Firm*—Dressler, Rockey, Milnamow & Katz

[57] ABSTRACT

A new and distinct cultivar of American black walnut (*Juglans nigra L.*) that is of medium size and has a good level of inherit resistance to anthracnose and other foliar diseases. The tree is a very heavy nut producer with a fairly consistent bearing habit.

6 Drawing Sheets

BACKGROUND OF THE INVENTION

This invention relates to a new and distinct variety of American black walnut tree (*Juglans nigra L.*).

In 1971, a variety of seedlings were obtained from the Missouri State Nursery in Licking along with additional seedlings and were planted in a plantation in Green County, Mo. The seedlings obtained from the Missouri State Nursery were approximately one year old and were labeled as "super seedlings" or "nursery run". As the trees developed and began to bear fruit, I recognized that the parent tree of this invention had improved characteristics. My interest and experience with American black walnut trees led me to realize that this tree was a unique and distinct development.

REPRODUCTION

Subsequently in 1990, I asexually reproduced the tree of the present invention taking scions from the parent tree and grafting these on to an unpatented American black walnut tree stock in Cedar County, Mo. The asexual reproductions ran true to the parent tree and to each other in all respects.

The botanical details of this new and distinct variety of American black walnut tree will not be described using data collected from the parent tree over a significant period of time.

DETAILED DESCRIPTION OF THE INVENTION

Figure 1:
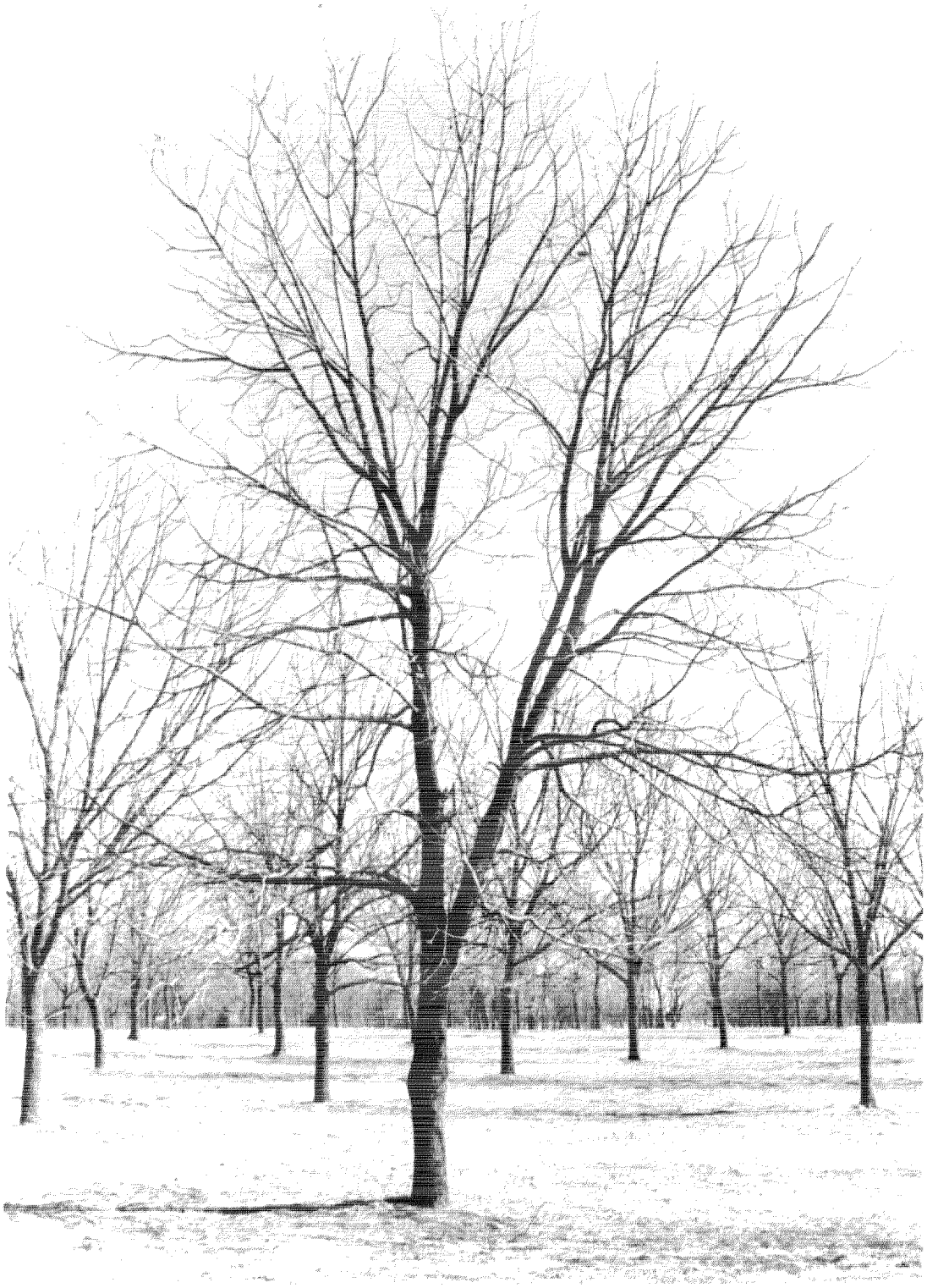
FIG. 1 is a photograph showing the timber form of parent tree of this invention at age 25.
Figure 2:
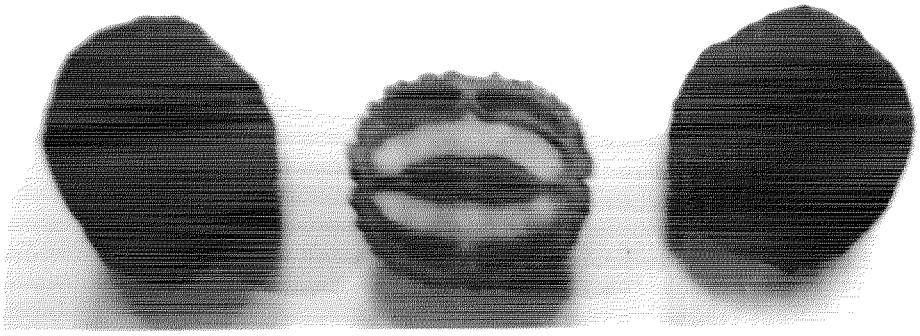
FIG. 2 is a photograph showing the nuts from the parent tree of this invention.

Tree: The tree is of medium size when compared to other black walnut trees of this species and exhibits medium to strong growth. The tree is very productive and has a large open-grown crown with a multiple twig/branching characteristic. The tree is approximately 48 feet tall, has a diameter of 14.7 inches at breast height (dbh) and a spread of approximately 36 feet. Although the tree started heavy nut production at a later age than most producers, it has in recent years become a very heavy producer with a fairly consistant bearing habit.

Trunk: The trunk of the tree is like that of other black walnut trees of this species. The bark is deeply grooved but not to extremes. The old bark is moderate to thin in thickness, is gray in color and is grooved but not deeptly fissured. In contrast, the new bark is gray to light brown to gray in color, has a smooth to split texture and is moderate to thin in thickness.

Branches: The form of the branches is the same as other black walnut trees of this species. The tree does not have any bad branch angles. The tree has multiple twig and branch characteristics and the branches have a smooth to split texture.

Stems: The stems are like the stems of other black walnut trees of this species. The stems have hair and are light gray to light brown in color. The light gray to light brown pubesence lasts most of the first year.

Leaves: The tree has an abundant quantity of leaves which are arranged in a pinnately compound fashion. The leaves are approximately 35 to 48 cm in length and approximately 18 to 22 cm in width. There are approximately 14–18 dark green leaflets per leaf which are approximately 6 to 12 cm in length and 2.5 to 3.5 cm in width. While the leaflets ar lanceolate in shape, they are very pointed at the apices and rounded at the base. Furthermore, the leaflets have a serrated margin and venation that is typical of that found in black walnut trees of this species. The central portion of the leaf has the widest and largest leaflets. The leaves are retained into the fall. The leaves also tend to exhibit very light anthracnose injury.

Leafing date: The tree exhibits late leafing unlike other black walnut trees of this species. The leafing occurs from April 25–May 10.

Inflorescence: The tree is precocious. Pistillate and staminate flowers are usually produced early, within 8 to 10 years. One to three pistillate flowers are present per bearing site on the flowering tip. The female flower is not inconspicuous. The first female bloom is between May 1–May 10. The peak female bloom is between May 10–May 15. The last female bloom is between May 15–May 20. The first male bloom is between April 25–May 1. The peak male bloom is between April 30–May 10. The last male bloom is May 10–May 15. The first pollen is shed between May 1–May 6. Generally, the pollen is shed for approximately 8–11 days. The last pollen shed is May 10–May 15. The length of the female flower is ⅜–⅝ inch and the length of the male flower is 3–4 inches. The male and female flowers are not unlike the typical black walnut flower for this species.

Husk: The husk is generally rounded with protrusions at each end with no sutures. The surface of the husk is somewhat rough. Prior to harvest, the husk is dark to light green in color. At harvest, the husk may be light green to yellow in color. The husk does not open freely and does not have a splitting tendency.

Figure 3:
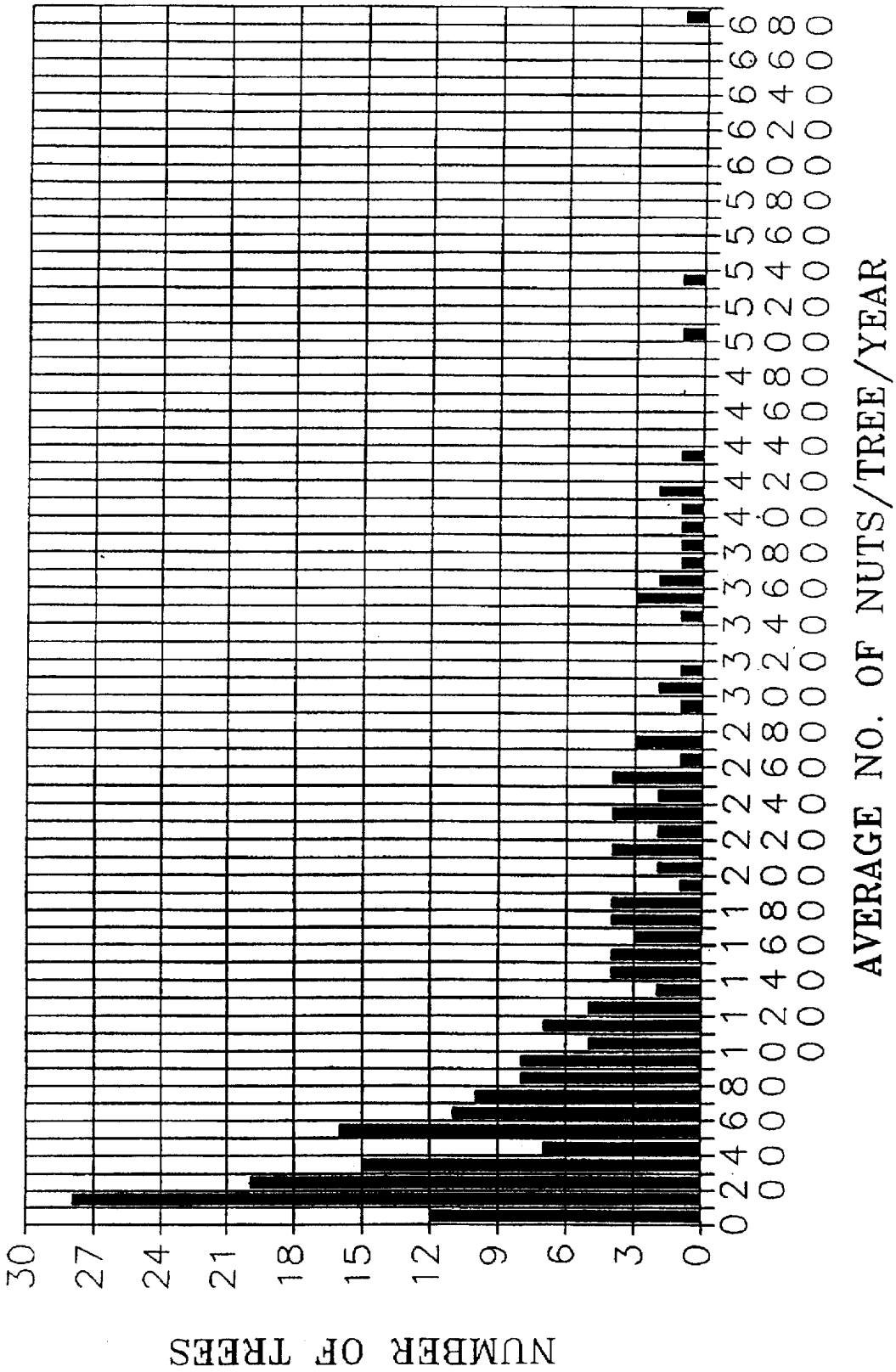
FIG. 3 is a bar graph of the walnut bearing characteristic of the parent tree of this invention with 215 other black walnut trees grown in the same block/area.

Nut: The nut is medium in size and has an average length of 1.4 inches and an average width of approximately 1.3 inches taking an average of the width from cheek to cheek and from suture to suture. The average weight of the nut (dry in shell) is 15.5 grams and the number of nuts per ounce is 0.52. The nut is rectangular in shape with terminal extensions and has a rough/corrugated texture. Additionally, the nut is light brown in color and has an inner shell and outer shell. The shell has a irregular to smooth texture. The percentage of kernal to nut is 25.7%. FIG. 3 depicts all the trees growing in the block/area where the parent tree is growing. The 216 black walnut tree were originally planted in 1971 in upland, limestone derived soil and spaced 40'×40' apart from one another at Mr. Charles Sheppard's farm in Green County, Mo. FIG. 3 illustrates the huge variation in nut bearing capabilities of the species. The parent tree of this invention is represented by the short vertical bar on the far right side of the graph, and produces an average of 680 nuts per year (the nuts were harvested from 1983–1992).

Kernel: The kernel has an irregular shape, in size and is easily extracted from the nut. The lobe has an average length of 2.5 cm, an average width of 1.5 cm and an average thickness of 0.5 cm. The kernel is light brown in color and has a mostly smooth texture. The average weight of a kernel in a nut is 4.0 grams.

Growing conditions: Upland, limestone derived soil.

Harvest: The nuts are generally ready for harvest between September 25–October 15. No special conditions are needed for harvesting. The nuts are simply picked up by hand as they mature and fall to the ground naturally. Once harvested, the nuts are counted and the husk removed. The nuts are then weighed and air dried.

Disease resistance: This late leafing tree appears to have a good level of inherent resistance to anthracnose and other foliar diseases.

Isoelectric focusing: Isoelectric focusing was conducted on the parent tree of this invention as well as the parent tree of HPC-148 (U.S. Ser. No. 08/617,047) and HPC-120 (U.S. Ser. No. 08/618,280) by Isolab, Inc., Akron, Ohio, to develop an enzyme profile for these trees. The procedure used is described below.

*Sample preparation.*—Ten individual leaves from the parent tree was homogenized with an enzyme extraction solution. The samples were allowed to incubate at 4°–8° C. overnight. The samples were then configured and the resulting supernant was ready for electrophoresis in a pH gradient.

*Isoelectric focusing.*—The supernant was run through a broad-ranged (pH-3–10) HyPure Gel (Isolab, Inc., Akron, Ohio). After protein separatoin, isozyme staining was performed for selected proteins. The stains used were selective for the following 8 enzymes: acid phosphatase, malic enzyme, diaphorase, esterase, alcohol dehydrogenase, isocitric dehydrogenase, malate dehydrogenase and peroxidase. These enzymes were selected because they are useful for showing the differences between varieties. Acid phosphatase, malic enzyme and diaphorase were chosen for further examination because these three enzymes gave the most intensity.

Figure 4:
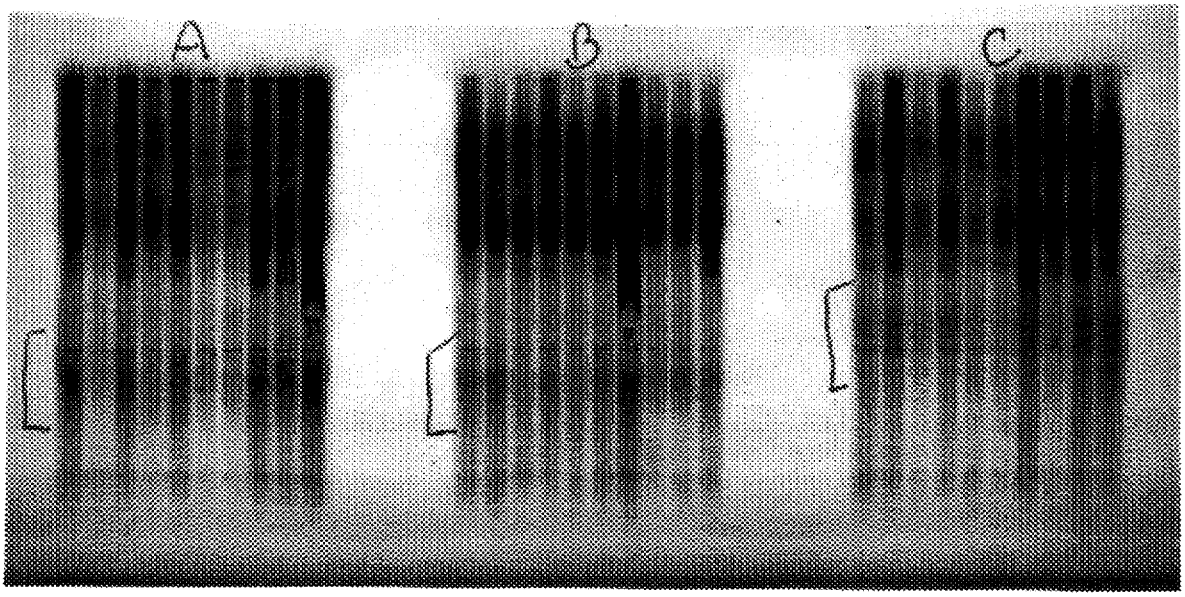
FIG. 4 contains three electrophoresis gels resulting from isoelectric focusing. The enzyme acid phosphatase was used to establish an enzyme pattern for the parent tree of this invention and other trees.

*Results.*—As shown in FIG. 4, the parent tree of HPC-148 and the parent tree of HPC-120 gave the same pattern for the acid phosphatase. The parent tree of this invention gave a different pattern. The pattern tree of this invention is shown in C, HPC-148 is shown in A and HPC-120 is shown in B. Each lane represents an individual leaf sample.

Figure 5:
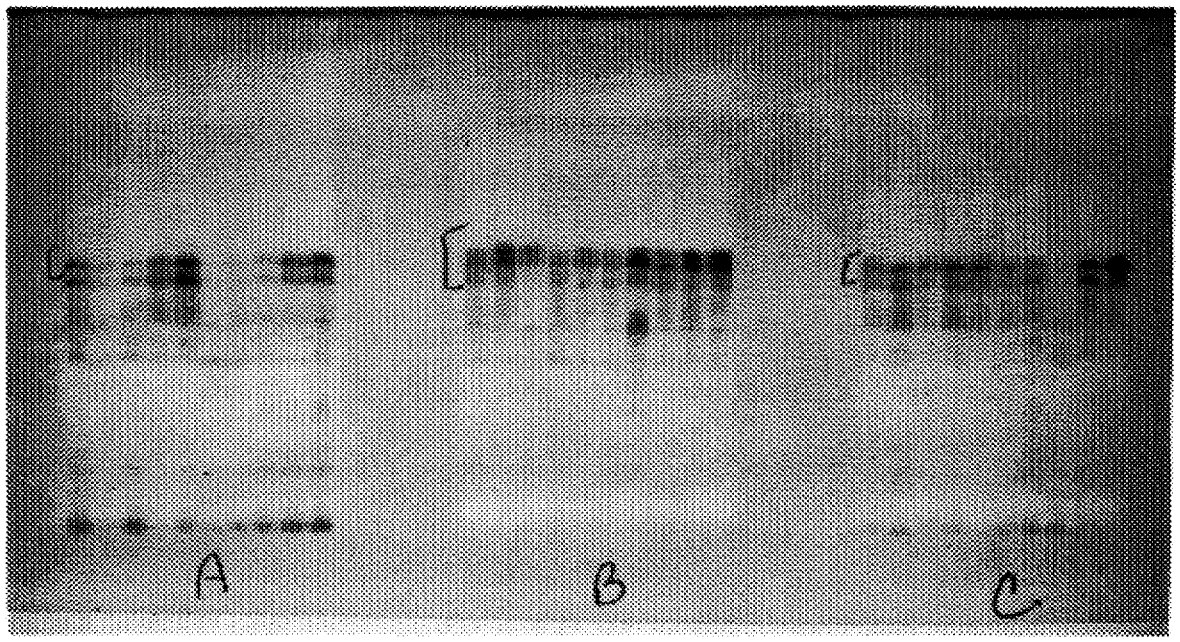
FIG. 5 contains three electrophoresis gels resulting from isoelectric focusing. The enzyme used was the malic enzyme.

As shown in FIG. 5, the parent tree of this invention and the parent tree of HPC-148 gave single pattern when tested with the male enzyme. The parent tree of HPC-120 gave a double pattern. The parent tree of this invention is shown in C, HPC-148 is shown in A and HPC-120 is shown in B.

Figure 6:
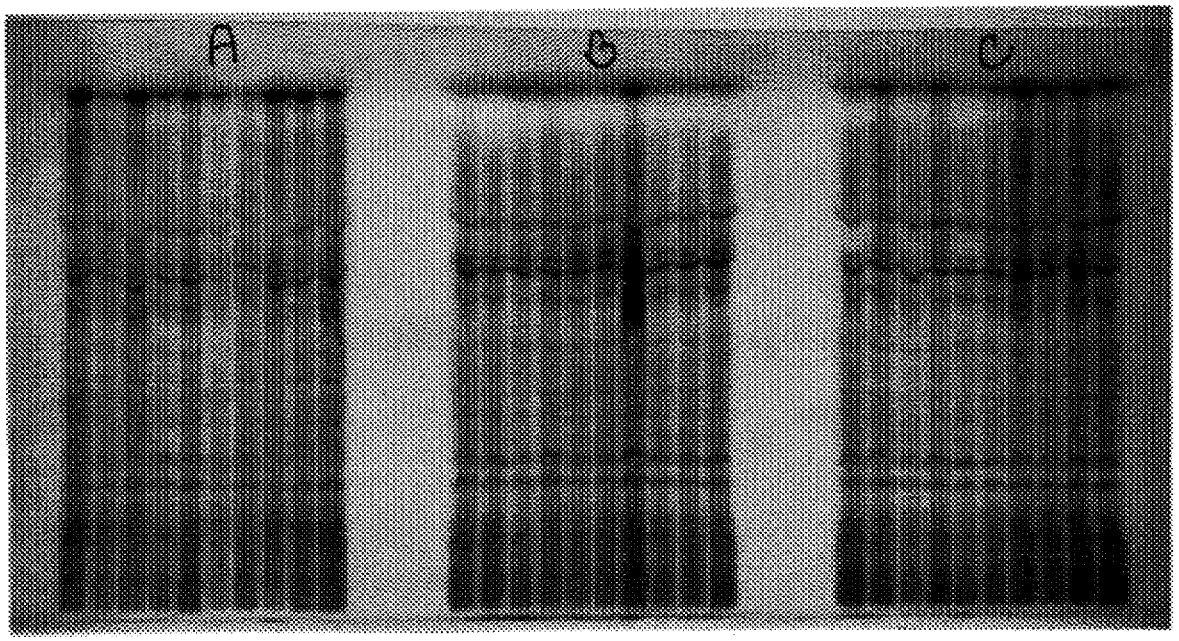
FIG. 6 contains three electrophoresis gels resulting from isoelectric focusing. The enzyme used was diaphorase.

As shown in FIG. 6, all of the trees gave the same exact enzyme pattern with for the diaphorase. The parent tree of this invention is shown in C, HPC-148 is shown in A and HPC-120 is shown in B.

Therefore, these three trees can be differentiated using the acid phosphatase and the malic enzyme patterns.

I claim:

1. The new and distinct variety of black walnut tree herein described and illustrated and identified by the characteristics above.

* * * * *